(12) United States Patent
Kimura et al.

(10) Patent No.: US 7,872,083 B2
(45) Date of Patent: Jan. 18, 2011

(54) POLYMER AND COSMETIC PREPARATION

(75) Inventors: Tomohiko Kimura, Yokohama (JP); Akira Noda, Yokohama (JP); Hiroaki Yokoyama, Sodegaura (JP); Takuji Nozawa, Sodegaura (JP); Akio Suzuki, Sodegaura (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 521 days.

(21) Appl. No.: 11/917,830

(22) PCT Filed: Jun. 23, 2006

(86) PCT No.: PCT/JP2006/312571

§ 371 (c)(1),
(2), (4) Date: Dec. 17, 2007

(87) PCT Pub. No.: WO2006/137511

PCT Pub. Date: Dec. 28, 2006

(65) Prior Publication Data

US 2009/0123408 A1    May 14, 2009

(30) Foreign Application Priority Data

Jun. 23, 2005    (JP)    ............................. 2005-182977

(51) Int. Cl.
*C08F 226/04* (2006.01)
(52) U.S. Cl. ................. 526/312; 424/70.11; 424/70.15; 424/70.16; 424/70.17; 510/119; 510/159
(58) Field of Classification Search ................. 526/312; 424/70.11, 70.15, 70.16, 70.17; 510/119, 510/159
See application file for complete search history.

(56) References Cited

U.S. PATENT DOCUMENTS

| | | | |
|---|---|---|---|
| 5,750,099 A * | 5/1998 | Yoshihara et al. | 424/70.17 |
| 5,981,456 A * | 11/1999 | Tartakovsky et al. | 510/220 |
| 6,949,498 B2 * | 9/2005 | Murphy et al. | 510/327 |
| 7,012,054 B2 * | 3/2006 | Binder et al. | 510/327 |
| 2006/0030513 A1 * | 2/2006 | Binder et al. | 510/515 |
| 2007/0166250 A1 * | 7/2007 | Hiwatashi et al. | 424/61 |
| 2008/0286218 A1 * | 11/2008 | Giroud et al. | 424/61 |

FOREIGN PATENT DOCUMENTS

EP    1847172 A1    10/2007

OTHER PUBLICATIONS

Japanese Patent Abstract Publication No. 2001-064678 published Mar. 13, 2001, one page.
Japanese Patent Abstract Publication No. 2003-073257 published Mar. 12, 2003, one page.
Partial English translation of Japanese Publication No. S62-4799 published Jan. 10, 1987, three pages.
Supplementary European Search Report for 06767221 mailed May 8, 2009, four pages.

* cited by examiner

*Primary Examiner*—Bernard Lipman
(74) *Attorney, Agent, or Firm*—Rankin, Hill & Clark LLP

(57) ABSTRACT

The present invention provides a novel polymer that can impart a moisturized feeling to the hair and skin after use. A polymer comprising an amphoteric monomer represented by the following general formula (I) and a cationic monomer represented by the following general formula (II) as the essential constituent monomers:

[Formula 1]

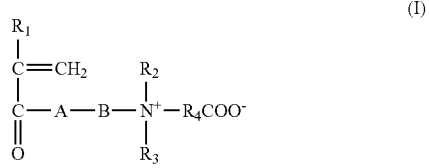

(wherein, $R_1$ represents a hydrogen atom or a methyl group; $R_2$ and $R_3$ each independently represent an alkyl or alkoxy group having 1 to 4 carbon atoms, a cycloalkyl group having 3 to 6 carbon atoms, a phenyl group, or a —$(CH_2CH_2O)_nR_7$ group (n is an integer of 1 to 50; and $R_7$ represents a hydrogen atom or an alkyl or alkoxy group having 1 to 4 carbon atoms, a cycloalkyl group having 3 to 6 carbon atoms, or a phenyl group); $R_4$ represents an alkylene group having 1 to 3 carbon atoms; A represents an oxygen atom or $NR_8$ ($R_8$ represents a hydrogen atom or an alkyl or alkoxy group having 1 to 4 carbon atoms, a phenyl group, or a —$(CH_2CH_2O)_nR_9$ group (n is an integer of 1 to 50; $R_9$ represents a hydrogen atom, an alkyl or alkoxy group having 1 to 4 carbon atoms, a cycloalkyl group having 3 to 6 carbon atoms, or a phenyl group)); and B represents an alkylene group having 1 to 4 carbon atoms), and

[Formula 2]

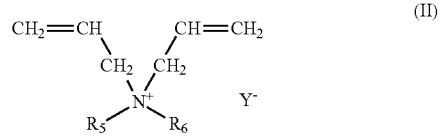

(wherein, $R_5$ and $R_6$ each independently represent a hydrogen atom or an alkyl or alkoxy group having 1 to 4 carbon atoms; and $Y^-$ represents a monovalent inorganic or organic anion).

20 Claims, No Drawings

POLYMER AND COSMETIC PREPARATION

RELATED APPLICATIONS

This application claims priority from Japanese Patent Application No. 2005-182977 filed on Jun. 23, 2005, the disclosure of which is incorporated by reference herein.

FIELD OF THE INVENTION

The present invention relates to a polymer and a cosmetic preparation, in particular to a hair and skin cleanser.

BACKGROUND OF THE INVENTION

Generally, feeling during use and after use is quite important for cosmetics. For example in the case of hair and skin cleansers, in addition to its inherent function of cleansing force, the quality of the foams during cleansing and the feeling of hair and skin after cleansing are also important. As for the foam quality, creamy foams with smaller air bubbles tend to be popular. Alternatively as for the feeling of hair and skin, cleansers containing a surfactant higher in cleansing force often lead to undesired defatting of the skin and hair. Thus, there is a need for a cleanser giving a moisturized and comfortable feeling.

Therefore, studies for improvement in the foam quality and the feeling by adding various polymers to a cleanser base are under progress. For example, patent document 1 discloses a cleanser containing a cationic polymer, and patent documents 2 and 3 disclose a cleanser containing a cationic polymer and an amphoteric polymer constituted from an anionic monomer, a cationic monomer and a nonionic monomer.

[Patent Document 1] Japanese Unexamined Patent Publication No. S62-4799

[Patent Document 2] Japanese Unexamined Patent Publication No. 2001-64678

[Patent Document 3] Japanese Unexamined Patent Publication No. 2003-73257

DISCLOSURE OF THE INVENTION

Problem to be Solved by the Invention

However, any of the cleansers above did not show enough moisturized feeling on the skin and hair after use.

An object of the present invention is to provide a novel polymer that can impart a moisturized feeling to the hair and skin after use.

Means to Solve the Problem

After intensive studies under the circumstances above, the inventors have found that it was possible to obtain a cosmetic preparation drastically improved in moisturized feeling by using a polymer obtained by polymerization of a specific amphoteric monomer and a specific cationic monomer. Also use of the polymer in hair or skin cleanser was effective in improving foaming, and thus, completed the present invention.

Thus, a first aspect of the present invention is a polymer comprising an amphoteric monomer represented by the following general formula (I) and a cationic monomer represented by the following general formula (II) as the essential constituent monomers:

[Formula 1]

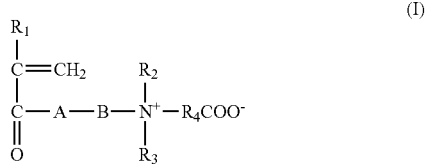

(wherein, $R_1$ represents a hydrogen atom or a methyl group; $R_2$ and $R_3$ each independently represent an alkyl or alkoxy group having 1 to 4 carbon atoms, a cycloalkyl group having 3 to 6 carbon atoms, a phenyl group, or a $-(CH_2CH_2O)_nR_7$ group (n is an integer of 1 to 50; and $R_7$ represents a hydrogen atom or an alkyl or alkoxy group having 1 to 4 carbon atoms, a cycloalkyl group having 3 to 6 carbon atoms, or a phenyl group); $R_4$ represents an alkylene group having 1 to 3 carbon atoms; A represents an oxygen atom or $NR_8$ ($R_8$ represents a hydrogen atom or an alkyl or alkoxy group having 1 to 4 carbon atoms, a phenyl group, or a $-(CH_2CH_2O)_nR_9$ group (n is an integer of 1 to 50; $R_9$ represents a hydrogen atom, an alkyl or alkoxy group having 1 to 4 carbon atoms, a cycloalkyl group having 3 to 6 carbon atoms, or a phenyl group)); and B represents an alkylene group having 1 to 4 carbon atoms), and

[Formula 2]

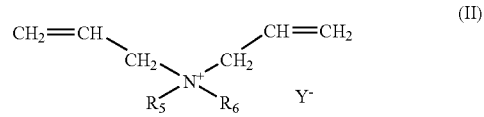

(wherein, $R_5$ and $R_6$ each independently represent a hydrogen atom or an alkyl or alkoxy group having 1 to 4 carbon atoms; and $Y^-$ represents a monovalent inorganic or organic anion).

In the polymer above, the molar ratio of the cationic monomer to the amphoteric monomer is preferably 1:9 to 9:1.

In the polymer above, the average molecular weight of the polymer is preferably 10,000 or more and 1,000,000 or less.

A second aspect of the present invention is a cosmetic preparation comprising the polymer containing an amphoteric monomer represented by general formula (I) and a cationic monomer represented by general formula (II) as essential constituent monomers.

The cosmetic preparation preferably contains an anionic surfactant additionally.

The cosmetic preparation is preferably a hair cleanser or a skin cleanser.

Effect of the Invention

The polymer according to the present invention, which comprises a specific amphoteric monomer and a specific cationic monomer as essential constituent monomers, can impart a moisturized feeling to hair and skin after use.

BEST MODE FOR CARRYING OUT THE INVENTION

Hereinafter, preferable embodiments of the present invention will be described in detail.

Polymer

The polymer according to the present invention comprises an amphoteric monomer represented by the following general formula (I) and a cationic monomer represented by the following general formula (II) as its constituent monomers.

[Formula 3]

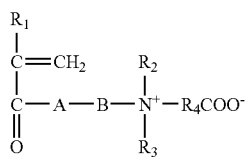

(wherein, $R_1$ represents a hydrogen atom or a methyl group; $R_2$ and $R_3$ each independently represent an alkyl or alkoxy group having 1 to 4 carbon atoms, a cycloalkyl group having 3 to 6 carbon atoms, a phenyl group, or a $(CH_2CH_2O)_nR_7$ group (n is an integer of 1 to 50; and $R_7$ represents a hydrogen atom or an alkyl or alkoxy group having 1 to 4 carbon atoms, a cycloalkyl group having 3 to 6 carbon atoms, or a phenyl group); $R_4$ represents an alkylene group having 1 to 3 carbon atoms; A represents an oxygen atom or $NR_8$ ($R_8$ represents a hydrogen atom or an alkyl or alkoxy group having 1 to 4 carbon atoms, a phenyl group, or a —$(CH_2CH_2O)_nR_9$ group (n is an integer of 1 to 50; $R_9$ represents a hydrogen atom, an alkyl or alkoxy group having 1 to 4 carbon atoms, a cycloalkyl group having 3 to 6 carbon atoms, or a phenyl group)); and B represents an alkylene group having 1 to 4 carbon atoms).

[Formula 4]

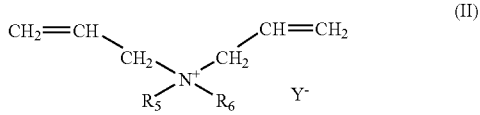

(wherein, $R_5$ and $R_6$ each independently represent a hydrogen atom or an alkyl or alkoxy group having 1 to 4 carbon atoms; and $Y^-$ represents a monovalent inorganic or organic anion).

The amphoteric monomer represented by the general formula (I) is a N-substituted aminoalkylacrylamide betaine, a N-substituted aminoalkylmethacrylamide betaine, a N-substituted aminoalkylacrylate betaine or a N-substituted aminoalkylmethacrylate betaine.

In general formula (I), the substituent groups of nitrogen $R_2$ and $R_3$ each represent an alkyl or alkoxy group having 1 to 4 carbon atoms, a cycloalkyl group having 3 to 6 carbon atoms, a phenyl group, or a —$(CH_2CH_2O)_nR_7$ group (n is an integer of 1 to 50; and $R^7$ represents a hydrogen atom or an alkyl or alkoxy group having 1 to 4 carbon atoms, a cycloalkyl group having 3 to 6 carbon atoms, or a phenyl group).

The alkyl or alkoxy group having 1 to 4 carbon atoms may be linear or branched and part of it may be substituted with a hydroxyl group or a fluorine atom. Examples of the alkyl groups having 1 to 4 carbon atoms include methyl, ethyl, propyl, butyl, 2-hydroxyethyl, 2-hydroxypropyl, trifluoromethyl, trifluoroethyl and the like. Examples of the alkoxy groups having 1 to 4 carbon atoms include methoxy, ethoxy, propoxy, isopropoxy, butoxy, tert-butoxy and the like.

Examples of the cycloalkyl groups having 3 to 6 carbon atoms include cyclopropyl, cyclobutyl, cyclopentyl, cyclohexyl and the like. $R_2$ and $R_3$ may be the same as and different from each other.

In general formula (I), $R_4$ represents an alkylene group having 1 to 3 carbon atoms. An alkylene group having four or more carbon atoms is higher in hydrophobicity, leading to deterioration of moisturizing action. The alkylene group having 1 to 3 carbon atoms may be linear or branched, and part of it may be substituted with a hydroxyl group or a fluorine atom. Examples thereof include methylene, ethylene, propylene, isopropylene, 2-hydroxyethylene, 2-hydroxypropylene, difluoromethylene, difluoroethylene and the like.

In general formula (I), A represents an oxygen atom or a group represented by $NR_8$. The substituent group of nitrogen $R_8$ represents a hydrogen atom or an alkyl or alkoxy group having 1 to 4 carbon atoms, a phenyl group, or a —$(CH_2CH_2O)_nR_9$ group (n is an integer of 1 to 50; and $R_9$ represents a hydrogen, an alkyl or alkoxy group having 1 to 4 carbon atoms, a cycloalkyl group having 3 to 6 carbon atoms, or a phenyl group). The alkyl or alkoxy group having 1 to 4 carbon atoms may be linear or branched, and part of it may be substituted with a hydroxyl group or a fluorine atom. Examples of the alkyl groups having 1 to 4 carbon atoms include methyl, ethyl, propyl, butyl, 2-hydroxyethyl, 2-hydroxypropyl, trifluoromethyl, trifluoroethyl and the like. Examples of the alkoxy groups having 1 to 4 carbon atoms include methoxy, ethoxy, propoxy, isopropoxy, butoxy, tert-butoxy and the like.

Examples of the cycloalkyl group having 3 to 6 carbon atoms include cyclopropyl, cyclobutyl, cyclopentyl, cyclohexyl and the like. $R_2$ and $R_3$ may be the same as and different from each other.

In general formula (I), B represents an alkylene group having 1 to 4 carbon atoms. Typical examples thereof include methylene, ethylene, propylene, iso-propylene, butylene and the like.

Examples of the amphoteric monomers for use in the present invention include N,N-dimethylaminopropyl (meth) acrylamide acetate betaine, N,N-dimethylaminoethyl (meth) acrylate acetate betaine, and the like. N,N-dimethylaminopropyl (meth)acrylamide acetate betaine is preferable.

The cationic monomer represented by general formula (II) is a dialkyldiallylammonium salt. In general formula (II), the substituent groups of quaternary ammonium nitrogen $R_5$ and $R_6$ each represent a hydrogen atom or an alkyl or alkoxy group having 1 to 4 carbon atoms.

The alkyl or alkoxy group having 1 to 4 carbon atoms may be linear or branched, and part of it may be substituted with a hydroxyl group or a fluorine atom. Examples of the alkyl groups having 1 to 4 carbon atoms include methyl, ethyl, propyl, butyl, 2-hydroxyethyl, 2-hydroxypropyl, trifluoromethyl, trifluoroethyl and the like. Examples of the alkoxy group having 1 to 4 carbon atoms include methoxy, ethoxy, propoxy, isopropoxy, butoxy, tert-butoxy and the like.

In general formula (II), $Y^-$ is not particularly limited, if it is a monovalent inorganic or organic anion that can form a quaternary ammonium salts. Examples of the monovalent inorganic anions include chloride ion, fluoride ion, iodide ion, and the like, and examples of the monovalent organic anions include sulfate ion, acetate ion, benzenesulfonate ion, phosphate ion, and the like. $R_5$ and $R_6$ may be the same as and different from each other.

Examples of the cationic monomers for use in the present invention include dimethyldiallylammonium chloride, diethyldiallylammonium chloride, dipropyldiallylammonium chloride, dimethyldiallylammonium sulfate, diethyldiallylammonium sulfate, dipropyldiallylammonium sulfate and the like. Among them, dimethyldiallylammonium chloride is particularly favorable.

The polymer according to the present invention can be prepared by polymerizing the amphoteric monomer and the cationic monomer by a known polymerization method.

Examples of the polymerization methods include homogeneous solution polymerization, heterogeneous solution polymerization, emulsion polymerization, negative phase emulsion polymerization, bulk polymerization, suspension polymerization, precipitation polymerization, and the like. For example in the case of the homogeneous solution polymerization, a polymer according to the present invention is obtained by dissolving respective monomers at a suitable molar ratio in a solvent, adding a radical polymerization initiator, and stirring the mixture while heated under nitrogen environment.

In the present invention, a polymer having a desirable monomer molar ratio can be obtained easily by adjusting the molar ratio of the respective raw material monomers.

The solvent used during polymerization is not particularly limited, if it dissolves or disperses respective monomers, and examples thereof include water, alcohol solvents such as methanol, ethanol, propyl alcohol, isopropyl alcohol, and butyl alcohol; hydrocarbon solvents such as hexane, heptane, octane, isooctane, decane, and liquid paraffin; ether solvents such as dimethylether, diethylether, and tetrahydrofuran; ketone solvents such as acetone and methylethylketone; ester solvents such as methyl acetate, ethyl acetate, and butyl acetate; chloride-based solvents such as methylene chloride, chloroform, and carbon tetrachloride; dimethylformamide, diethylformamide, dimethylsulfoxide, dioxane, and the like. These solvents may be used alone or as a mixture of two or more. Normally, it is desirable to select a solvent having a boiling point higher than the polymerization initiation temperature of the polymerization initiator.

The polymerization initiator is not particularly limited, if it has a potential to initiate radical polymerization. Examples thereof include peroxides such as benzoyl peroxide; azo compounds such as azobisisobutylonitrile (AIBN) and dimethyl 2,2'-azobis(isobutyrate); as well as persulfuric acid-based polymerization initiators such as potassium persulfate and ammonium persulfate. The polymerization temperature is preferably not lower than the polymerization initiation temperature of each polymerization initiator. For example, it is normally about 70° C., when a peroxide-based polymerization initiator is used. The polymerization may be initiated, for example, in photochemical reaction or by radiation ray irradiation, instead of using such a polymerization initiator.

The polymerization period is not particularly limited and may be varied arbitrarily according to the desirable molecular weight of the polymer, but is normally 2 to 24 hours. A shorter reaction time may lead to residual of unreacted monomers and insufficient increase of the molecular weight.

The molar ratio of the monomers for the polymer according to the present invention is not particularly limited, but the ratio of the cationic monomer to the amphoteric monomeric molar ratio is preferably 1:9 to 9:1. The molar ratio is more preferably 1:9 to 5:5 and particularly preferably about 4:6. A polymer at a ratio outside the range above has properties not like a copolymer but more like a homopolymer, giving insufficient moisturizing action when blended in a cosmetic preparation.

The weight-average molecular weight of the polymer according to the present invention is preferably 10,000 or more and 1,000,000 or less. A polymer having a molecular weight of less than 10,000 is hard to appear polymer-like properties, giving insufficient moisturizing action when blended in a cosmetic preparation. Alternatively, a polymer having a molecular weight of more than 1,000,000 also tends to deteriorate in moisturizing action.

In preparation of the polymer according to the present invention, the order of adding the respective monomers is not particularly limited, and thus, the addition may be blockwise addition or random addition, but normally, a polymer of random addition is obtained.

A typical example of the polymer according to the present invention, dimethyldiallylammonium chloride/N,N-dimethylaminopropylacrylamide acetate betaine copolymer, is shown in the following general formula (III).

[Formula 5]

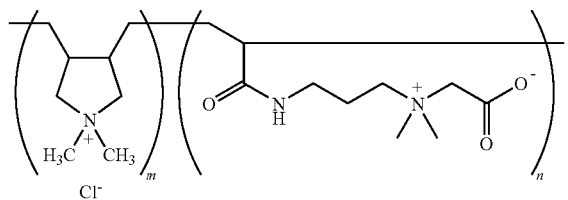

(III)

In general formula (III), m and n each represent the molar ratios respectively of the cationic monomer (dimethyldiallylammonium chloride) and the amphoteric monomer (N,N-dimethylpropylacrylamide acetate betaine) with respect to the total amount of constituent monomers; m is 0.01 to 0.99; and n is 0.99 to 0.01. Preferably, m is 0.1 to 0.9, and n is 0.9 to 0.1; and more preferably, m is 0.15 to 0.5, and n is 0.50 to 0.85.

The polymer according to the present invention may be a terpolymer containing an nonionic monomer in addition to the essential constituent monomers above. The nonionic monomer for copolymerization is, for example, an acrylamide monomer or the like.

Cosmetic Preparation

The cosmetic preparation according to the present invention is characterized by containing a polymer having an amphoteric monomer represented by the following general formula (I) and a cationic monomer as the essential constituent monomers.

[Formula 6]

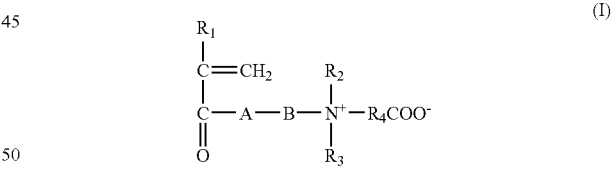

(I)

(wherein, $R_1$ represents a hydrogen atom or a methyl group; $R_2$ and $R_3$ each independently represent an alkyl or alkoxy group having 1 to 4 carbon atoms, a cycloalkyl group having 3 to 6 carbon atoms, a phenyl group, or a —$(CH_2CH_2O)_nR_7$ group (n is an integer of 1 to 50; and $R_7$ represents a hydrogen atom or an alkyl or alkoxy group having 1 to 4 carbon atoms, a cycloalkyl group having 3 to 6 carbon atoms, or a phenyl group); $R_4$ represents an alkylene group having 1 to 3 carbon atoms; A represents an oxygen atom or $NR_8$ ($R_8$ represents a hydrogen atom or an alkyl or alkoxy group having 1 to 4 carbon atoms, a phenyl group, or a —$(CH_2CH_2O)_nR_9$ group (n is an integer of 1 to 50; $R_9$ represents a hydrogen atom, an alkyl or alkoxy group having 1 to 4 carbon atoms, a cycloalkyl group having 3 to 6 carbon atoms, or a phenyl group)), and B represents an alkylene group having 1 to 4 carbon atoms).

The amphoteric monomer represented by the general formula (I) is a N-substituted aminoalkyl (meth)acrylamide betaine or a N-substituted aminoalkyl (meth)acrylate betaine.

In general formula (I), the substituent groups of nitrogen $R_2$ and $R_3$ each represent an alkyl or alkoxy group having 1 to 4 carbon atoms, a cycloalkyl group having 3 to 6 carbon atoms, a phenyl group, or a —$(CH_2CH_2O)_nR_7$ group (n is an integer of 1 to 50; and $R^7$ represents a hydrogen atom or an alkyl or alkoxy group having 1 to 4 carbon atoms, a cycloalkyl group having 3 to 6 carbon atoms, or a phenyl group).

The alkyl or alkoxy group having 1 to 4 carbon atoms may be linear or branched, and part of it may be substituted with a hydroxyl group or a fluorine atom. Examples of the alkyl groups having 1 to 4 include methyl, ethyl, propyl, butyl, 2-hydroxyethyl, 2-hydroxypropyl, trifluoromethyl, trifluoroethyl and the like. Examples of the alkoxy groups having 1 to 4 carbon atoms include methoxy, ethoxy, propoxy, isopropoxy, butoxy, tert-butoxy and the like.

Examples of the cycloalkyl groups having 3 to 6 carbon atoms include cyclopropyl, cyclobutyl, cyclopentyl, cyclohexyl and the like. $R_2$ and $R_3$ may be the same as and different from each other.

In general formula (I), $R_4$ represents an alkylene group having 1 to 3 carbon atoms. An alkylene group having four or more carbon atoms is higher in hydrophobicity, leading to deterioration of moisturizing action. The alkylene group having 1 to 3 carbon atoms may be linear or branched, and part of it may be substituted with a hydroxyl group or a fluorine atom. Examples thereof include methylene, ethylene, propylene, isopropylene, 2-hydroxyethylene, 2-hydroxypropylene, difluoromethylene, difluoroethylene and the like.

In general formula (I), A represents an oxygen atom or a group represented by $NR_8$. The substituent group of nitrogen $R_8$ represents a hydrogen atom, an alkyl or alkoxy group having 1 to 4 carbon atoms, phenyl group, or, a $(CH_2CH_2O)_n R_9$ group (n is an integer of 1 to 50; and $R_9$ represents a hydrogen, an alkyl or alkoxy group having 1 to 4 carbon atoms, a cycloalkyl group having 3 to 6 carbon atoms, or a phenyl group). The alkyl or alkoxy group having 1 to 4 carbon atoms may be linear or branched, and part of it may be substituted with a hydroxyl group or a fluorine atom. Examples of the alkyl groups having 1 to 4 carbon atoms include methyl, ethyl, propyl, butyl, 2-hydroxyethyl, 2-hydroxypropyl, trifluoromethyl, trifluoroethyl and the like. Examples of the alkoxy groups having 1 to 4 carbon atoms include methoxy, ethoxy, propoxy, isopropoxy, butoxy, tert-butoxy and the like.

Examples of the cycloalkyl groups having 3 to 6 carbon atoms include cyclopropyl, cyclobutyl, cyclopentyl, cyclohexyl and the like. $R_2$ and $R_3$ may be the same as and different from each other.

Also in general formula (I), B represents an alkylene group having 1 to 4 carbon atoms. Typical examples thereof include methylene, ethylene, propylene, iso-propylene, butylene and the like.

Examples of the amphoteric monomers for use in the invention include N,N-dimethylaminopropyl (meth)acrylamide acetate betaine, N,N-dimethylaminoethyl (meth)acrylate acetate betaine and the like, and preferable is N,N-dimethylaminopropyl (meth)acrylamide acetate betaine.

Examples of the cationic monomers include N,N-dialkyldiallylammonium salts, dialkylaminoethyl methacrylates, methacryloxyethyltrimethylammonium salts, methacryloxyethyltrimethylammonium methylsulfate, acryloyloxyethyltrimethylammonium salts, dimethylaminopropyl methacrylamide, methacrylamide propyltrimethylammonium salts and the like.

As the cationic monomer, a cationic monomer represented by the following general formula (II), dialkyldiallylammonium salt, is particularly preferable from the point of smaller odor change at various pH.

[Formula 7]

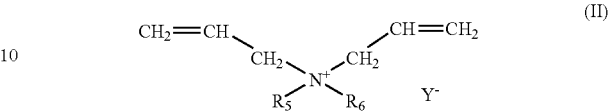

(wherein, $R_5$ and $R_6$ each independently represent a hydrogen atom or an alkyl or alkoxy group having 1 to 4 carbon atoms; and $Y^-$ represents a monovalent inorganic or organic anion).

In general formula (II), the substituent group of quaternary ammonium nitrogen $R_5$ and $R_6$ each represent a hydrogen atom or an alkyl or alkoxy group having 1 to 4 carbon atoms. The alkyl or alkoxy group having 1 to 4 carbon atoms may be linear or branched, and part of it may be substituted with a hydroxyl group or a fluorine atom.

Examples of the alkyl groups having 1 to 4 carbon atoms include methyl, ethyl, propyl, butyl, 2-hydroxyethyl, 2-hydroxypropyl, trifluoromethyl, trifluoroethyl and the like. Examples of the alkoxy groups having 1 to 4 carbon atoms include methoxy, ethoxy, propoxy, isopropoxy, butoxy, tert-butoxy and the like.

In general formula (II), $Y^-$ is not particularly limited, if it is a monovalent inorganic or organic anion that can form a quaternary ammonium salts, and examples of the monovalent inorganic anions include chloride ion, fluoride ion, iodide ion, and the like, and examples of the monovalent organic anions include sulfate ion, acetate ion, benzenesulfonate ion, phosphate ion, and the like. $R_5$ and $R_6$ may be the same as and different from each other.

Examples of the cationic monomers represented by general formula (II) include dimethyldiallylammonium chloride, diethyldiallylammonium chloride, dipropyldiallylammonium chloride, dimethyldiallylammonium sulfate, diethyldiallylammonium sulfate, dipropyldiallylammonium sulfate and the like. Among them, particularly favorable is dimethyldiallylammonium chloride.

The blending amount of the polymer in the cosmetic preparation according to the present invention may be determined arbitrarily, but is preferably 0.01 to 10 mass %, more preferably 0.1 to 3 mass %, with respect to the total amount of the cosmetic preparation. A polymer blending amount of less than 0.01 mass % may lead to insufficient improvement in skin moisturizing action, while a blending amount of more than 10 mass % may cause excessive stickiness of the skin.

In the cosmetic preparation according to the present invention, use of an anionic surfactant in combination with the polymer is favorable from the point of moisturized feeling on hair and skin after use. It is also favorable from the point of foaming efficiency in the case of a hair and skin cleanser. It is attributed to the interaction between the anionic surfactant and the cationic regions of the polymer.

The anionic surfactant is not particularly limited, but favorable for use is one or more compounds selected from fatty acid soaps, long-chain acyl ether carboxylate salts, polyoxyethylene alkylether sulfate salts, long-chain acyl amino acid salts, and long-chain acyl lower-alkyl taurine salts, and use of a fatty acid soap is particularly preferable.

Examples of the fatty acid soaps include sodium laurate, sodium myristate, sodium palmitate, sodium stearate, potassium laurate, potassium myristate, potassium palmitate, potassium stearate, and the like; examples of the long-chain acylether carboxylate salts include POE-laurylether carboxylate salts and the like; examples of the polyoxyethylene alkylether sulfate salts include polyoxyethylene laurylether sulfate salts and the like; examples of the long chain acylamino acid salts include monosodium N-lauroylglutamate, disodium N-stearoylglutamate, L-monosodium N-myristoylglutamate, and the like; and examples of the long-chain acyl lower alkyl taurine salts include N-lauroylmethyltaurine sodium, N-stearoylmethyltaurine sodium and the like.

The blending amount of the anionic surfactant is not particularly limited, but preferably 1.0 to 60 mass %, more preferably 5.0 to 40 mass %, with respect to the total amount of the cosmetic preparation. An anionic surfactant blending amount of less than 1.0 mass % may lead to insufficient addition effect, while a blending amount of more than 60 mass % to saturation of the advantageous effect of addition.

The cosmetic preparation according to the present invention may contain, in addition to the components above, other components normally used in cosmetic and pharmaceutical preparations in the range that does not impair the advantageous effects of the present invention. Examples of the blendable components include moisturizing agent, powder component, liquid oil, solid fat, wax, hydrocarbon oil, higher fatty acid, higher alcohol, synthetic ester oil, silicone oil, cationic surfactant, amphoteric surfactant, nonionic surfactant, natural water-soluble polymer, semisynthetic water-soluble polymer, synthetic water-soluble polymer, thickener, ultraviolet absorbent, metal ion scavenger, lower alcohol, polyvalent alcohol, monosaccharide, oligosaccharide, polysaccharide, amino acid, organic amine, polymer emulsion, pH adjuster, antioxidant, antioxidant aid, antiseptic, anti-inflammatory, whitener, various extracts, activator, blood circulation accelerator, antiseborrheic agent, antiinflammatory agent and the like.

The formulation of the cosmetic preparation according to the present invention is also arbitrary, and may be cream, emulsion, solution, solubilized system, powder dispersion, water-oil bilayer system, water-oil-powder trilayer system, or the like.

Hereinafter, the present invention will be described in detail with reference to examples, but it should be understood that the present invention is not restricted thereby.

The blending amount is expressed by mass % with respect to the entire system to which the component is added, unless otherwise indicated. The monomer composition in each polymer is shown by the molar ratio of each monomer in the total constituent monomers. The blending amount of each polymer is expressed by net weight.

Example 1

First, the preparative methods for the polymers according to the present invention will be described.

Preparative Example 1

64.6 g (400 mmol) of dimethyldiallylammonium chloride and 128.5 g (600 mmol) of N,N-dimethylaminopropylacrylamide acetate betaine were used to obtain a desirable dimethyldiallylammonium chloride/N,N-dimethylaminopropylacrylamide acetate betaine copolymer.

Preparative Example 2

75.9 g (400 mmol) of diethyldiallylammonium chloride and 128.5 g (600 mmol) of N,N-dimethylaminopropylacrylamide acetate betaine were used to obtain a desirable diethyldiallylammonium chloride/N,N-dimethylaminopropylacrylamide acetate betaine copolymer.

Hereinafter, the evaluation criteria in the present invention are as follows (1) Foam Quality The foam quality of each facial cleanser was evaluated in a practical use test by ten professional panellers according to the following evaluation criteria, and the average point was calculated.

5 points: creamy 4 points: slightly creamy 3 points: normal 2 points: less creamy 1 point: not creamy (2) Moisturized Feeling The moisturized feeling on skin after cleansing of each facial cleanser was evaluated in a practical use test by ten professional panellers according to the following evaluation criteria, and the average point was calculated.

5 points: moisturized 4 points: slightly moisturized 3 points: normal 2 points: less moisturized 1 point: not moisturized Practical use tests concerning the items above were conducted, by using each of the facial cleansers respectively containing various polymers. The blending compositions of the facial cleansers and the evaluation results are summarized in the following Table 1.

TABLE 1

|  | Example | | | | | |
| --- | --- | --- | --- | --- | --- | --- |
|  | 1-1 | 1-2 | 1-3 | 1-4 | 1-5 | 1-6 |
| Polymer of Preparative Example 1 | 0.5 | — | — | — | — | — |
| Polydimethyldiallylammonium chloride (*1) | — | 0.5 | — | — | — | — |

TABLE 1-continued

|  | Example | | | | | |
| --- | --- | --- | --- | --- | --- | --- |
|  | 1-1 | 1-2 | 1-3 | 1-4 | 1-5 | 1-6 |
| Dimethyldiallylammonium chloride/acrylamide copolymer (*2) | — | — | 0.5 | — | 0.25 | — |
| Acrylic acid/dimethyldiallylammonium chloride/acrylamide copolymer (*3) | — | — | — | 0.5 | 0.25 | — |
| Glycerin | 15.0 | 15.0 | 15.0 | 15.0 | 15.0 | 15.0 |
| Sorbit solution | 20.0 | 20.0 | 20.0 | 20.0 | 20.0 | 20.0 |
| Polyethylene glycol | 5.0 | 5.0 | 5.0 | 5.0 | 5.0 | 5.0 |
| Lauric acid | 5.0 | 5.0 | 5.0 | 5.0 | 5.0 | 5.0 |
| Myristic acid | 12.0 | 12.0 | 12.0 | 12.0 | 12.0 | 12.0 |
| Palmitic acid | 5.0 | 5.0 | 5.0 | 5.0 | 5.0 | 5.0 |
| Stearic acid | 10.0 | 10.0 | 10.0 | 10.0 | 10.0 | 10.0 |
| Potassium hydroxide | 6.0 | 6.0 | 6.0 | 6.0 | 6.0 | 6.0 |
| Ion-exchange water | Balance | Balance | Balance | Balance | Balance | Balance |
| (1) Foam quality | 4.6 | 2.5 | 3.5 | 3.8 | 3.0 | 2.0 |
| (2) Moisturized feeling | 4.8 | 3.6 | 4.0 | 3.6 | 3.8 | 3.0 |

(*1): ME polymer H40W ™ (manufactured by Toho Chemical Industry Co., Ltd.)
(*2): ME polymer 09W ™ (manufactured by Toho Chemical Industry Co., Ltd.)
(*3): ME polymer T-343 ™ (manufactured by Toho Chemical Industry Co., Ltd.)

In the facial cleanser of Example 1-6 containing no polymer, the foam quality during cleansing was unfavorable and also the skin moisturized feeling after cleansing was not obtained.

On the other hand, the facial cleanser of Example 1-2 including a cationic polymer containing only a cationic monomer (dimethyldiallylammonium chloride) as its constituent monomer and that of Example 1-3 including a cationic polymer containing a cationic monomer (dimethyldiallylammonium chloride) and a nonionic monomer (acrylamide) as its constituent monomers were improved to some extent both in the foam quality and moisturized feeling, but the advantageous effects were far from satisfactory. In addition, the preparation of Example 1-2 easily caused precipitation.

The facial cleanser of Example 1-4 including an amphoteric polymer containing an anionic monomer (acrylic acid), a cationic monomer (dimethyldiallylammonium chloride) and a nonionic monomer (acrylamide) as its constituent monomers and the facial cleanser of Example 1-5 in combination of a cationic polymer and an amphoteric polymer were improved to some extent in foam quality, but the moisturized feeling after use was insufficient.

In contrast, the facial cleanser of Example 1-1 including a polymer according to the present invention containing an amphoteric monomer (N,N-dimethylaminopropylacrylamide acetate betaine) and a cationic monomer (dimethyldiallylammonium chloride) as its constituent monomers was found to be extremely superior in the foam quality during cleansing and also drastically improved in skin moisturized feeling after cleansing.

The results indicate that use of the polymer containing an amphoteric monomer and a cationic monomer as its constituent monomers is effective in improving foam quality and moisturizing action specifically.

The advantageous effect above is an effect only found when a polymer containing a cationic monomer and an amphoteric monomer, which contains anionic and cationic groups in the same molecule, as its constituent monomers is used. The effect is not found when the amphoteric monomer is replaced with an anionic monomer and a cationic monomer.

Example 2

Facial cleansers each containing the polymer different in monomer ratio were compared, for estimation of the favorable molar ratio of the amphoteric monomer to the cationic monomer in the polymer according to the present invention. Each polymer was a copolymer of dimethyldiallylammonium chloride and N,N-dimethylaminopropylacrylamide acetate betaine (weight-average molecular weight: 400,000). The polymers prepared according to the method of Preparative Example 1.

In the present invention, a polymer having a desirable monomer molar ratio can be obtained easily by adjusting the molar ratio of the respective raw material monomers.

The blending composition of the facial cleansers and the evaluation results are summarized in the following Table 2.

TABLE 2

|  |  |  | Example | | | | | | |
| --- | --- | --- | --- | --- | --- | --- | --- | --- | --- |
|  |  |  | 2-1 | 2-2 | 2-3 | 2-4 | 2-5 | 2-6 | 2-7 |
| Polymer | Molar ratio | 1:9 | 0.2 | — | — | — | — | — | — |
|  |  | 4:6 | — | 0.2 | — | — | — | — | — |
|  |  | 5:5 | — | — | 0.2 | — | — | — | — |
|  |  | 6:4 | — | — | — | 0.2 | — | — | — |
|  |  | 9:1 | — | — | — | — | 0.2 | — | — |

TABLE 2-continued

| | Example | | | | | | |
|---|---|---|---|---|---|---|---|
| | 2-1 | 2-2 | 2-3 | 2-4 | 2-5 | 2-6 | 2-7 |
| 10:0 | — | — | — | — | — | 0.2 | — |
| 0:10 | — | — | — | — | — | — | 0.2 |
| Glycerin | 15.0 | 15.0 | 15.0 | 15.0 | 15.0 | 15.0 | 15.0 |
| Sorbit solution | 20.0 | 20.0 | 20.0 | 20.0 | 20.0 | 20.0 | 20.0 |
| Polyethylene glycol | 5.0 | 5.0 | 5.0 | 5.0 | 5.0 | 5.0 | 5.0 |
| Lauric acid | 5.0 | 5.0 | 5.0 | 5.0 | 5.0 | 5.0 | 5.0 |
| Myristic acid | 12.0 | 12.0 | 12.0 | 12.0 | 12.0 | 12.0 | 12.0 |
| Palmitic acid | 5.0 | 5.0 | 5.0 | 5.0 | 5.0 | 5.0 | 5.0 |
| Stearic acid | 10.0 | 10.0 | 10.0 | 10.0 | 10.0 | 10.0 | 10.0 |
| Potassium hydroxide | 6.0 | 6.0 | 6.0 | 6.0 | 6.0 | 6.0 | 6.0 |
| Ion-exchange water | Balance | Balance | Balance | Balance | Balance | Balance | Balance |
| (1) Foam quality | 4.4 | 4.6 | 4.4 | 4.2 | 4.2 | 2.5 | 2.8 |
| (2) Moisturized feeling | 4.6 | 4.8 | 4.5 | 4.2 | 4.4 | 3.6 | 3.6 |

As shown in Table 2 above, the preparations of Examples 2-6 and 2-7 containing a non-copolymer were unsatisfactory in foam quality and moisturized feeling. In addition, the preparations containing a polymer of dimethyldiallylammonium chloride and N,N-dimethylaminopropylacrylamide acetate betaine at a molar ratio in the range of 1:9 to 9:1 were superior in foam quality and moisturizing action. The preparations at a molar ratio 1:9 to 5:5 (Examples 2-1 to 2-5) were preferable, and the preparation at a molar ratio of close to 4:6 (Example 2-2) were particularly preferable.

It can be confirmed by the results that the molar ratio of the amphoteric monomer to the cationic monomer in the polymer according to the present invention is preferably 1:9 to 9:1, more preferably 1:9 to 5:5, and particularly preferably close to 4:6.

Example 3

Subsequently, facial cleansers each containing the polymer different in weight-average molecular weight were prepared and evaluated for determination of the favorable weight-average molecular weight of the polymer. Each polymer was a copolymer of dimethyldiallylammonium chloride and N,N-dimethylaminopropylacrylamide acetate betaine (molar ratio: 4:6) that was prepared by a method similar to Preparative Example 1.

The weight-average molecular weight was determined by gel permeation chromatography (hereinafter, referred to as GPC). The GPC measuring condition is shown as follows:

GPC Measuring Condition

Column:

OHpak SB-804HQ

OHpak SB-803HQ

OHpak SB-802HQ (all, manufactured by SHOWA DENKO K.K.)

Column temperature: 40° C.

Detector: RI

Solvent: 0.25 M acetic acid+0.05 M sodium chloride (pH: 3.5)

Flow rate: 0.7 ml/minute

Sample concentration: 0.5%

Injection: 50 μl

Standard: pullulan (Shodex STANDARD P-82, manufactured by SHOWA DENKO K.K.)

The blending composition of the facial cleanser in each Example and the evaluation results are summarized in Table 3.

TABLE 3

| | | | Example | | | | |
|---|---|---|---|---|---|---|---|
| | | | 3-1 | 3-2 | 3-3 | 3-4 | 3-5 |
| Polymer | Molecular weight | 5000 | 0.5 | — | — | — | — |
| | | 10000 | — | 0.5 | — | — | — |
| | | 100000 | — | — | 0.5 | — | — |
| | | 1000000 | — | — | — | 0.5 | — |
| | | 3000000 | — | — | — | — | 0.5 |
| Glycerin | | | 15.0 | 15.0 | 15.0 | 15.0 | 15.0 |
| Sorbit solution | | | 20.0 | 20.0 | 20.0 | 20.0 | 20.0 |
| Polyethylene glycol | | | 5.0 | 5.0 | 5.0 | 5.0 | 5.0 |
| Lauric acid | | | 5.0 | 5.0 | 5.0 | 5.0 | 5.0 |
| Myristic acid | | | 12.0 | 12.0 | 12.0 | 12.0 | 12.0 |
| Palmitic acid | | | 5.0 | 5.0 | 5.0 | 5.0 | 5.0 |
| Stearic acid | | | 10.0 | 10.0 | 10.0 | 10.0 | 10.0 |
| Potassium hydroxide | | | 6.0 | 6.0 | 6.0 | 6.0 | 6.0 |
| Ion-exchange water | | | Balance | Balance | Balance | Balance | Balance |
| (1) Foam quality | | | 3.8 | 4.2 | 4.5 | 4.7 | 4.5 |
| (2) Moisturized feeling | | | 4.0 | 4.4 | 4.6 | 4.6 | 3.8 |

As shown in Table 3 above, the preparations containing a polymer having a weight-average molecular weight of 10,000 to 1,000,000 were particularly favorable in foam quality and moisturized feeling.

Hereinafter, other examples of the present invention will be described, but the present invention is not limited thereto.

Example 4

Facial Cleanser

|  | (mass %) |
|---|---|
| (1) Polymer of Preparative Example 1 | 0.5 |
| (2) Glycerin | 15.0 |
| (3) Polyethylene glycol 400 | 5.0 |
| (4) Lauric acid | 5.0 |
| (5) Myristic acid | 10.0 |
| (6) Palmitic acid | 10.0 |
| (7) Stearic acid | 15.0 |
| (8) Lauroylmethyltaurine sodium | 5.0 |
| (9) Fatty acid monoglyceride | 1.0 |
| (10) Polyglyceryl monolaurate | 1.0 |
| (11) Potassium hydroxide | 6.0 |
| (12) Ion-exchange water | Balance |
| (13) Perfume | q.s. |

(Manufacturing Process)

Ingredients (2) to (10) were added in (12), and the mixture was solubilized while heated at 75° C. After solubilization, the solution was neutralized with (11); (1) was added thereto; after the mixture was stirred thoroughly, (13) was added; and the mixture was cooled, to give a product.

The facial cleanser was extremely advantageous both in foam quality during cleansing and skin moisturized feeling after cleansing.

Example 5

Body Shampoo

|  | (mass %) |
|---|---|
| (1) Polymer of Preparative Example 1 | 0.5 |
| (2) Glycerin | 15.0 |
| (3) Polyethylene glycol 400 | 5.0 |
| (4) Lauric acid | 2.0 |
| (5) Myristic acid | 5.0 |
| (6) Palmitic acid | 5.0 |
| (7) Stearic acid | 7.0 |
| (8) Lauroylmethyltaurine sodium | 5.0 |
| (9) Sodium laurylglycol acetate | 1.0 |
| (10) Potassium hydroxide | 3.0 |
| (11) Cationized guar gum | 0.2 |
| (12) Ion-exchange water | Balance |
| (13) Perfume | q.s. |

(Manufacturing Process)

Ingredients (2) to (9) were added to (12), and the mixture was solubilized while heated at 75° C. After solubilization, the solution was neutralized with (10); (1) and (11) were added thereto; after thorough stirring, (13) was added; and the mixture was cooled, to give a product.

The body shampoo was extremely favorable both in foam quality during cleansing and skin moisturized feeling after cleansing.

Example 6

Shampoo

|  | (mass %) |
|---|---|
| (1) Polymer of Preparative Example 2 | 0.2 |
| (2) Polyoxyethylene laurylether sodium sulfate | 4.0 |
| (3) Polyoxyethylene laurylether triethanolamine sulfate | 1.0 |
| (4) Palm-oil fatty acid amide propyl betaine | 5.0 |
| (5) Polymer JR-400 (manufactured by Union Carbide) | 0.6 |
| (6) Citric acid | 0.05 |
| (7) Sodium chloride | 0.5 |
| (8) Sodium benzoate | q.s. |
| (9) Ion-exchange water | Balance |
| (10) Perfume | q.s. |

(Manufacturing Process)

Ingredients (2) to (8) were added to (9), and the mixture was solubilized while heated at 75° C. After stirring, (1) was added thereto; after the mixture was stirred thoroughly, (10) was added; and the mixture was cooled, to give a product.

The shampoo was extremely favorable both in foam quality during cleansing and hair moisturized feeling after cleansing.

Example 7

Hair Conditioner

|  | (mass %) |
|---|---|
| (1) Polymer of Preparative Example 2 | 0.5 |
| (2) Dimethylpolysiloxane | 0.2 |
| (3) Stearyl alcohol | 0.2 |
| (4) Behenyl alcohol | 1.0 |
| (5) Glycerin | 1.5 |
| (6) Octyl palmitate | 1.0 |
| (7) Polyoxyethylene stearylether | 0.2 |
| (8) Citric acid | 0.05 |
| (9) Paraoxybenzoate ester | q.s. |
| (10) Phenoxyethanol | q.s. |
| (11) Hydroxyethylcellulose | 0.1 |
| (12) Stearyltrimethylammonium chloride | 1.0 |
| (13) High-molecular-weight methylpolysiloxane | 1.5 |
| (14) Ion-exchange water | Balance |
| (15) Perfume | q.s. |

(Manufacturing Process)

Ingredients (2), (5) to (13) were added to (14), and the mixture was stirred thoroughly while heated at 75° C. After solubilization, (1) was added thereto while stirring; (15) was added finally; and the mixture was stirred in a homomixer and cooled, to give a product.

The hair conditioner was extremely favorable in hair moisturized feeling after use.

Example 8

Hair Styling Preparation

|  | (mass %) |
|---|---|
| (1) Polymer of Preparative Example 1 | 0.3 |
| (2) Volatile isoparaffin | 0.5 |
| (3) Ethanol | 10.0 |
| (4) Polyoxyethylene hydrogenated castor oil | 0.5 |
| (5) Polyoxyethylene-polyoxypropylene decylether | 0.5 |
| (6) *Eriobotryae* folium extract | 0.1 |
| (7) Yukafoamer SMTM (manufactured by Dia Chemco) | 10.0 |
| (8) Ion exchange | Balance |

Stock solution/propellant: 90/10

(Manufacturing Process)

Ingredients (1) to (7) were added to (8); and the mixture was stirred thoroughly, to give a product.

The hair styling preparation was extremely favorable in hair moisturized feeling after use.

Example 9

Skin Lotion

|  | (mass %) |
|---|---|
| (1) Polymer of Preparative Example 1 | 0.3 |
| (2) Ethyl alcohol | 5.0 |
| (3) Glycerin | 3.0 |
| (4) 1,3-Butylene glycol | 5.0 |
| (5) Polyoxyethylene polyoxypropylene decyltetradecylether | 0.2 |
| (6) Sodium hexametaphosphate | 0.03 |
| (7) Trimethylglycine | 1.0 |
| (8) Sodium polyaspartate | 0.1 |
| (9) α-Tocopherol 2-L-phosphate ascorbate diester, potassium salt | 0.1 |
| (10) Thiotaurine | 0.1 |
| (11) Green tea extract | 0.1 |
| (12) Peppermint extract | 0.1 |
| (13) Iris root extract | 0.1 |
| (14) HEDTA, trisodium salt | 0.1 |
| (15) Carboxyvinyl polymer | 0.03 |
| (16) Potassium hydroxide | 0.015 |
| (17) Phenoxyethanol | q.s. |
| (18) Ion-exchange water | Balance |
| (19) Perfume | q.s. |

(Manufacturing Process)

Ingredients (1) to (17) and (19) were added to (18), and the mixture was stirred thoroughly, to give a product.

The skin lotion was extremely favorable in skin moisturized feeling after use.

What is claimed is:

1. A polymer comprising an amphoteric monomer represented by the following general formula (I) and a cationic monomer represented by the following general formula (II) as the essential constituent monomers:

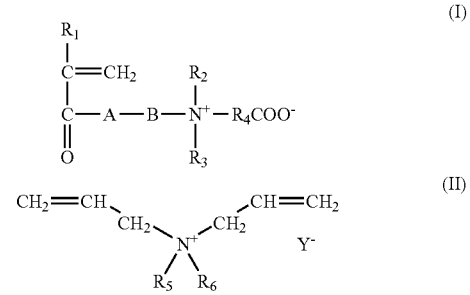

wherein, $R_1$ represents a hydrogen atom or a methyl group;
$R_2$ and $R_3$ each independently represent an alkyl or alkoxy group having 1 to 4 carbon atoms, a cycloalkyl group having 3 to 6 carbon atoms, a phenyl group, or a —$(CH_2CH_2O)_nR_7$ group, wherein n is an integer of 1 to 50; and $R_7$ represents a hydrogen atom, an alkyl group, or an alkoxy group having 1 to 4 carbon atoms, a cycloalkyl group having 3 to 6 carbon atoms, or a phenyl group;
$R_4$ represents an alkylene group having 1 to 3 carbon atoms;
A represents an oxygen atom or $NR_8$, wherein
$R_8$ represents a hydrogen atom, an alkyl group, or an alkoxy group having 1 to 4 carbon atoms, a phenyl group, or a —$(CH_2CH_2O)_nR_9$ group, wherein n is an integer of 1 to 50;
$R_9$ represents a hydrogen atom, an alkyl group, or an alkoxy group having 1 to 4 carbon atoms, a cycloalkyl group having 3 to 6 carbon atoms, or a phenyl group; and
B represents an alkylene group having 1 to 4 carbon atoms,
$R_5$ and $R_6$ each independently represent a hydrogen atom or an alkyl group, or an alkoxy group having 1 to 4 carbon atoms; and
$Y^-$ represents a monovalent inorganic or organic anion.

2. The polymer of claim 1, wherein the molar ratio of the cationic monomer to the amphoteric monomer is 1:9 to 9:1.

3. The polymer of claim 1, wherein the average molecular weight of the polymer is from 10,000 to 1,000,000.

4. A cosmetic preparation comprising the polymer of claim 1.

5. The cosmetic preparation of claim 4, further comprising an anionic surfactant.

6. A hair cleanser including the cosmetic preparation of claim 4.

7. The polymer of claim 2, wherein the average molecular weight of the polymer is from 10,000 to 1,000,000.

8. A skin cleanser including the cosmetic preparation of claim 4.

9. A hair cleanser including the cosmetic preparation of claim 5.

10. A skin cleanser including the cosmetic preparation of claim 5.

11. The polymer of claim 1, wherein at least one of $R_2$ and $R_3$ is an alkyl group selected from the group consisting of methyl, ethyl, propyl, butyl, 2-hydroxyethyl, 2-hydroxypropyl, trifluoromethyl, trifluoroethyl, and combinations thereof.

12. The polymer of claim 1, wherein at least one of $R_2$ and $R_3$ is an alkoxy group selected from the group consisting of methoxy, ethoxy, propoxy, isopropoxy, butoxy, tert-butoxy, and combinations thereof.

13. The polymer of claim 1, wherein at least one of $R_2$ and $R_3$ is a cycloalkyl group selected from the group consisting of cyclopropyl, cyclobutyl, cyclopentyl, cyclohexyl, and combinations thereof.

14. The polymer of claim 1, wherein $R_4$ is selected from the group consisting of methylene, ethylene, propylene, isopropylene, 2-hydroxyethylene, 2-hydroxypropylene, difluoromethylene, difluoroethylene, and combinations thereof.

15. The polymer of claim 1, wherein $Y^-$ is selected from the group consisting of chloride ion, fluoride ion, iodide ion, and the like, and examples of the monovalent organic anions include sulfate ion, acetate ion, benzenesulfonate ion, phosphate ion, and combinations thereof.

16. The polymer of claim 1, wherein the amphoteric monomer is selected from the group consisting of N,N-dimethylaminopropyl (meth)acrylamide acetate betaine, N,N-dimethylaminoethyl (meth)acrylate acetate betaine, and combinations thereof.

17. The polymer of claim 1, wherein the cationic monomer is selected from the group consisting of dimethyldiallylammonium chloride, diethyldiallylammonium chloride, dipropyldiallylammonium chloride, dimethyldiallylammonium sulfate, diethyldiallylammonium sulfate, dipropyldiallylammonium sulfate, and combinations thereof.

18. The polymer of claim 1, wherein the cationic monomer is dimethyldiallyl-ammonium chloride.

19. The polymer of claim 1, wherein the amphoteric monomer is N,N-dimethylaminopropylacrylamide acetate betaine and the cationic monomer is dimethyldiallylammonium chloride.

20. The polymer of claim 1, wherein the amphoteric monomer is N,N-dimethylaminopropylacrylamide acetate betaine and the cationic monomer is diethyldiallylammonium chloride.

* * * * *

UNITED STATES PATENT AND TRADEMARK OFFICE
CERTIFICATE OF CORRECTION

PATENT NO. : 7,872,083 B2
APPLICATION NO. : 11/917830
DATED : January 18, 2011
INVENTOR(S) : Tomohiko Kimura et al.

It is certified that error appears in the above-identified patent and that said Letters Patent is hereby corrected as shown below:

On the title page, Item (73) please insert below Shiseido Co., Ltd., Chuo-ku, Tokyo (JP), -- Toho Chemical Industry Co., Ltd., Chuo-ku, Tokyo (JP) --

Signed and Sealed this
Twelfth Day of July, 2016

Michelle K. Lee
*Director of the United States Patent and Trademark Office*